United States Patent [19]
Newell et al.

[11] Patent Number: 5,337,751
[45] Date of Patent: Aug. 16, 1994

[54] AIR FLOW CONTROL APPARATUS AND METHOD FOR AN AUTOMATIC BLOOD PRESSURE GAUGE

[75] Inventors: Scott W. Newell, Ipswich, Mass.; James Chickering, Newton, N.H.

[73] Assignee: Siemens Medical Electronics, Inc., Danvers, Mass.

[21] Appl. No.: 768,126

[22] Filed: Sep. 30, 1991

[51] Int. Cl.$^5$ .................... A61B 5/103; A61B 5/117
[52] U.S. Cl. .................................. 128/682; 128/668; 128/672; 128/677; 128/680
[58] Field of Search ......... 128/668, 672, 677, 680–683

[56] References Cited

U.S. PATENT DOCUMENTS

| | | |
|---|---|---|
| 3,581,734 | 6/1971 | Croslin et al. |
| 4,167,181 | 9/1979 | Lee |
| 4,178,918 | 12/1979 | Cornwell |
| 4,360,029 | 11/1982 | Ramsey, III |
| 4,378,807 | 4/1983 | Peterson et al. |
| 4,493,326 | 1/1985 | Hill et al. |
| 4,625,277 | 11/1986 | Pearce et al. |
| 4,660,567 | 4/1987 | Kaneko et al. |
| 4,735,321 | 4/1988 | Shirasaki |
| 4,872,461 | 10/1989 | Miyawaki ............... 128/682 |
| 4,949,710 | 8/1990 | Dorsett et al. |
| 4,969,466 | 11/1990 | Brooks .................. 128/680 |
| 5,052,397 | 10/1991 | Ramsey, III et al. ...... 128/682 |

FOREIGN PATENT DOCUMENTS 0208520  1/1987  European Pat. Off. ............ 128/682
2219209 12/1989  United Kingdom ............... 128/677

Primary Examiner—Randall L. Green
Assistant Examiner—P. Zuttarelli
Attorney, Agent, or Firm—Lawrence C. Edelman

[57] ABSTRACT

A deflation control system for the pressurized cuff of an automatic blood pressure gauge uses a pressure sensor to control solenoid valves. The solenoid valves are responsive to respective pulse signals having variable duty cycles to change their time-apertures and, thus, their flow rates. The duty cycles of the pulse signals are controlled to maintain a desired constant rate of pressure reduction in the cuff. A microprocessor generates a control value which determines the duty cycles of the pulse signals. This value is proportional to the initial volume of fluid in the cuff and to a predictive term which is provided from a table that is indexed by cuff pressure. This value is then augmented by a feedback term, generated by a feedback control loop to ensure an accurate deflation rate. The gain of the feedback loop is selected so that the feedback correction signals do not interfere with pulse signals modulating the pressure signal. The feedback term is normalized by the initial volume measurement. In addition, any new valve setting is applied in small steps over a time interval to further ensure smooth changes in the flow rate.

21 Claims, 6 Drawing Sheets

AIR FLOW CONTROL APPARATUS AND METHOD FOR AN AUTOMATIC BLOOD PRESSURE GAUGE

BACKGROUND OF THE INVENTION

The present invention is directed to apparatus and a method for automatically measuring the blood pressure of an individual and specifically to apparatus and a method for deflating a pressurized cuff to achieve a substantially constant rate of pressure reduction.

A conventional automatic blood pressure gauge includes a resilient inflatable cuff and an electric pump. The pump is controlled by a microprocessor to inflate the cuff with a fluid, such as air, to a preset pressure. In addition, this automatic gauge includes a pressure transducer that measures the instantaneous air pressure levels in the cuff. The pressure signal produced by the transducer is used to determine both the instantaneous air pressure of the cuff and the blood pressure pulse of the individual. This pressure signal is generally digitized and processed by the microprocessor to produce values representing the systolic and diastolic blood pressure measurements of the individual.

In operation, the cuff is affixed to the upper arm area of the patient and is then inflated to a pressure greater than the suspected systolic pressure, for example, 150 to 200 millimeters of mercury (mmHg). This pressure level collapses the main artery in the arm, effectively stopping any blood flow to the lower arm. Next, the cuff is deflated slowly and the transducer pressure signal is monitored to detect variations in cuff pressure caused by the patient's pulse, which is coupled into the cuff.

In general, the pulse component of the pressure signal has a relatively low amplitude, on the order of one percent of the total signal. A low level blood pressure pulse signal is first detected when the cuff pressure is released to a level which allows some blood flow into the collapsed artery. As the cuff deflation continues, the pulse signal rises in amplitude as more of the collapsed artery is allowed to expand in response to the pumping action of the heart. At some point, however, the pulse signal reaches a maximum amplitude level and then begins to decrease. This reduction in amplitude occurs as the artery becomes more fully open, the pumped blood flows without significantly expanding the artery, and the degree of mechanical coupling between the cuff and the arm of the patient is reduced.

In many automatic blood pressure measuring systems, the systolic and diastolic pressures are determined based on the pressure at which the pulse signal exhibits maximum amplitude. Such a system is described in U.S. Pat. No. 4,735,213 entitled DEVICE AND METHOD FOR DETERMINING SYSTOLIC BLOOD PRESSURE, which is hereby incorporated by reference for its teaching on automatic blood pressure gauges. In this system, the diastolic blood pressure is determined as the pressure, after the maximum pulse amplitude has been measured, at which the amplitude of the pulse signal is 70% of its maximum value.

Another exemplary system is described in U.S. Pat. No. 4,949,710 entitled METHOD OF ARTIFACT REJECTION FOR NONINVASIVE BLOOD-PRESSURE MEASUREMENT BY PREDICTION AND ADJUSTMENT OF BLOOD-PRESSURE DATA, which is hereby incorporated by reference for its teaching on automatic blood pressure gauges. In this system, the systolic and diastolic blood pressure levels are determined as the respective pressures corresponding to the amplitude of the pulse signal being 60% of the maximum value, prior to reaching the maximum value; and 80% of the maximum value, after reaching the maximum value.

FIG. 1a is a plot of the pressure signal versus time for a conventional automatic blood pressure gauge. This exemplary signal is generated by the cuff being quickly inflated to a preset initial pressure, greater than the systolic pressure, linearly deflated to a pressure below the diastolic pressure and then quickly deflated the rest of the way. The pulse signal is shown as a waveform superimposed on the linear deflation portion of the pressure curve. For clarity, the relative amplitude of this signal is exaggerated in the FIGURE.

FIG. 1b is a plot of the pulse signal shown in FIG. 1a, separated from the linearly decreasing pressure signal. FIG. 1c is a plot of the peak-to-peak amplitude of the signal shown in FIG. 1b. As illustrated by FIG. 1c, the amplitude of the pulse signal increases gradually until a time S, at which the linearly decreasing cuff pressure is the same as the systolic pressure of the patient. The amplitude of the pulse signal then increases at a greater rate from time S to time M at which the maximum amplitude is reached. The blood pressure level corresponding to this maximum pulse amplitude is commonly referred to as the mean arterial pressure (MAP). From this maximum amplitude, the pulse signal decreases rapidly to a time D, at which the cuff pressure is the diastolic pressure. The signal amplitude decreases from the point D until the cuff is entirely deflated.

In the second patent referenced above, a microcomputer is used to collect pressure data for a stepped reduction of cuff pressure. At each step, the cuff pressure is held constant and the signal provided by the pressure transducer is monitored for variations representing the blood pressure pulse signal. This data is then filtered to obtain a data value corresponding to a peak on the curve shown in FIG. 1b. The peak points collected over many pressure steps are fit to a curve, such as the one shown in FIG. 1c, which represents the peak-to-peak amplitudes of the waveform shown in FIG. 1b. The maximum pulse amplitude is determined from this curve.

In the referenced patent, the systolic blood pressure value is determined by locating the point S on the curve shown in FIG. 1c, prior to the occurrence of the maximum value, at which the pulse amplitude is 60% of the maximum value. The cuff pressure value which corresponds to this point is defined as the systolic pressure. Similarly, the diastolic pressure value is determined as the pressure value which corresponds to the time D in FIG. 1c. As described above, this time is after the occurrence of the maximum value of the pulse signal, when the amplitude of pulse signal is 80% of the maximum value.

In order to accurately determine the systolic and diastolic pressures of the patient, it is important to ensure that the sampling density of the points which define the curve 1b is substantially constant over the entire time that the blood pressure pulse signal is sampled. A relatively high sampling density is preferred to provide for accurate interpolation between samples and to decrease the effect of spurious "noise" pulses on the measured values. It is desirable to complete this task in a relatively short time period, so as to provide quick results and to minimize patient anxiety and discomfort.

Yet, this task is complicated by differences in blood pressure from person to person and in one person within a single day. For example, the systolic blood pressure of an individual may range between 90 mmHg and 180 mmHg in a single day between periods of sleep and periods of exercise. At the same time, the diastolic pressure may range between 50 mmHg and 110 mmHg. Furthermore, the blood pressure range of children and neonates is to be considered. Consequently, to ensure that accurate measurements are made for everyone who may be tested, it is desirable for the blood pressure gauge to release cuff pressure over a wide range of cuff pressure values in a relatively short time, either in controlled steps, such as in the second referenced patent, or at a substantially constant rate, such as in the first referenced patent.

The deflation of a fixed volume container through a fixed orifice area generates a pressure deflation curve which approximates a decaying exponential. One method to obtain a linear deflation rate is to use a valve having a controllable orifice area, for example, a needle valve which can be mechanically actuated to change its orifice area. Valves of this type, however, can be difficult to control.

The size of the valve orifice may be controlled using a closed loop control system, which changes the orifice area of the valve in a manner which holds the first derivative of the measured cuff pressure value substantially constant. To minimize errors and to ensure a short settling time from pressure transients caused, for example, by patient motion, it is desirable to use a control loop having a relatively short time constant.

This type of system, however, may affect the measurement of the blood pressure pulses. It may interpret the pulse signal as a transient pressure change and attempt to compensate for it in order to maintain a constant deflation rate. This action may undesirably reduce the amplitude of some of the pulses, thus changing the shape of the pulse amplitude curve shown in FIG. 1c.

One method for overcoming this problem is disclosed in the above referenced U.S. Pat. No. 4,949,710. In this patent, a microprocessor conditions a valve to reduce cuff pressure in predefined steps. At each step, multiple pulse amplitude measurements are taken. These measurements are processed to remove artifacts and the resulting values are used to generate an interpolated curve of pulse amplitude versus cuff pressure.

The deflation process is controlled by an algorithm which predicts a range of values that indicate valid pulse amplitudes. Based on a calculated pulse amplitude curve and the measured pulse amplitude at each step, this algorithm predicts the pulse amplitude for the next step. Any detected error between the actual and predicted pulse amplitude values for the next step indicates an artifact and the erroneous pulse is ignored.

Although the referenced patent includes a predictive algorithm, it is not used to control the deflation process directly, rather it is used for artifact detection.

SUMMARY OF THE INVENTION

The present invention is embodied in an automatic blood pressure measurement device in which an inflated cuff is deflated to achieve a controlled pressure reduction. This device uses a deflation valve which has a controllable flow setting. This flow setting is controlled using processing circuitry which relates the present measured cuff pressure to a predictive valve setting which will produce a desired flow rate. To maintain the desired deflation rate, the processing circuitry periodically monitors the cuff pressure and changes the flow setting of the valve to a new predictive setting based on the last measured cuff pressure value.

In accordance with another aspect of the invention, the system determines the initial volume of the cuff from the cuff pressure and the last measured inflation rate. This initial volume measurement is then used to predict the valve settings to achieve the desired deflation rate.

According to another aspect of the invention, the system includes a feedback control loop which continually monitors the cuff pressure and makes fine adjustments to the flow setting of the valve to reduce any deviations from the desired deflation rate. These deviations may occur, for example, due to inaccuracies in the flow characteristics of the valves or due to cuff volume changes caused by patient motion.

DETAILED DESCRIPTION OF THE INVENTION

Figure 1A:
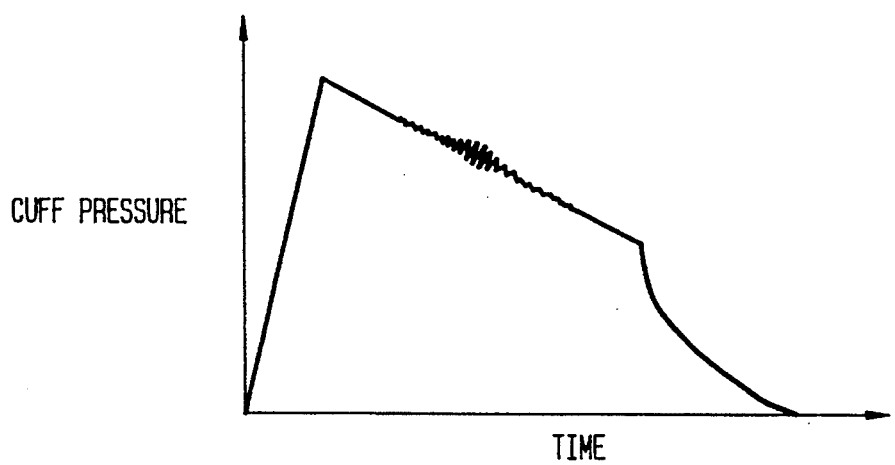
FIGS. 1a through 1c, labeled prior art, are graphs, showing measured pressure variations versus time, which are useful for describing the environment in which the present invention operates.
Figure 1B:
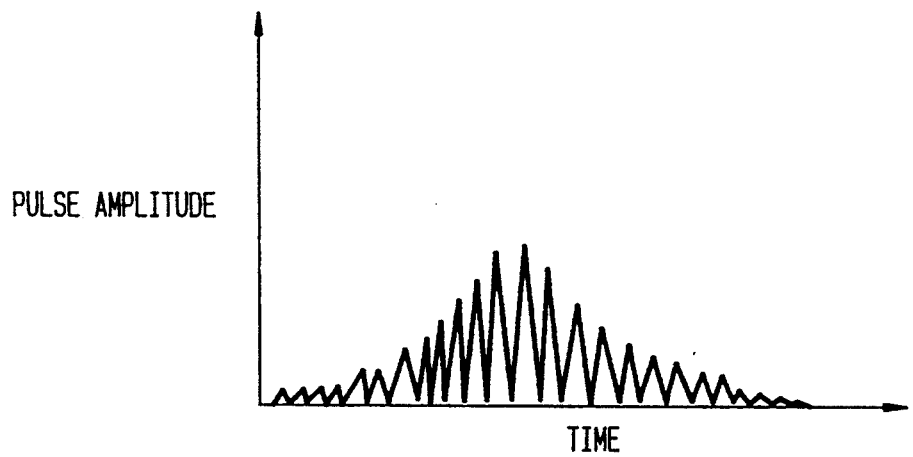
Figure 1C:
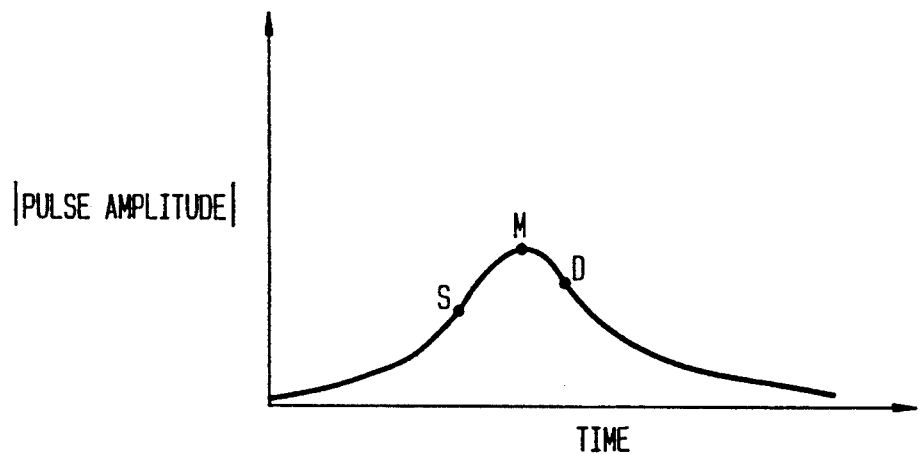
Figure 2:
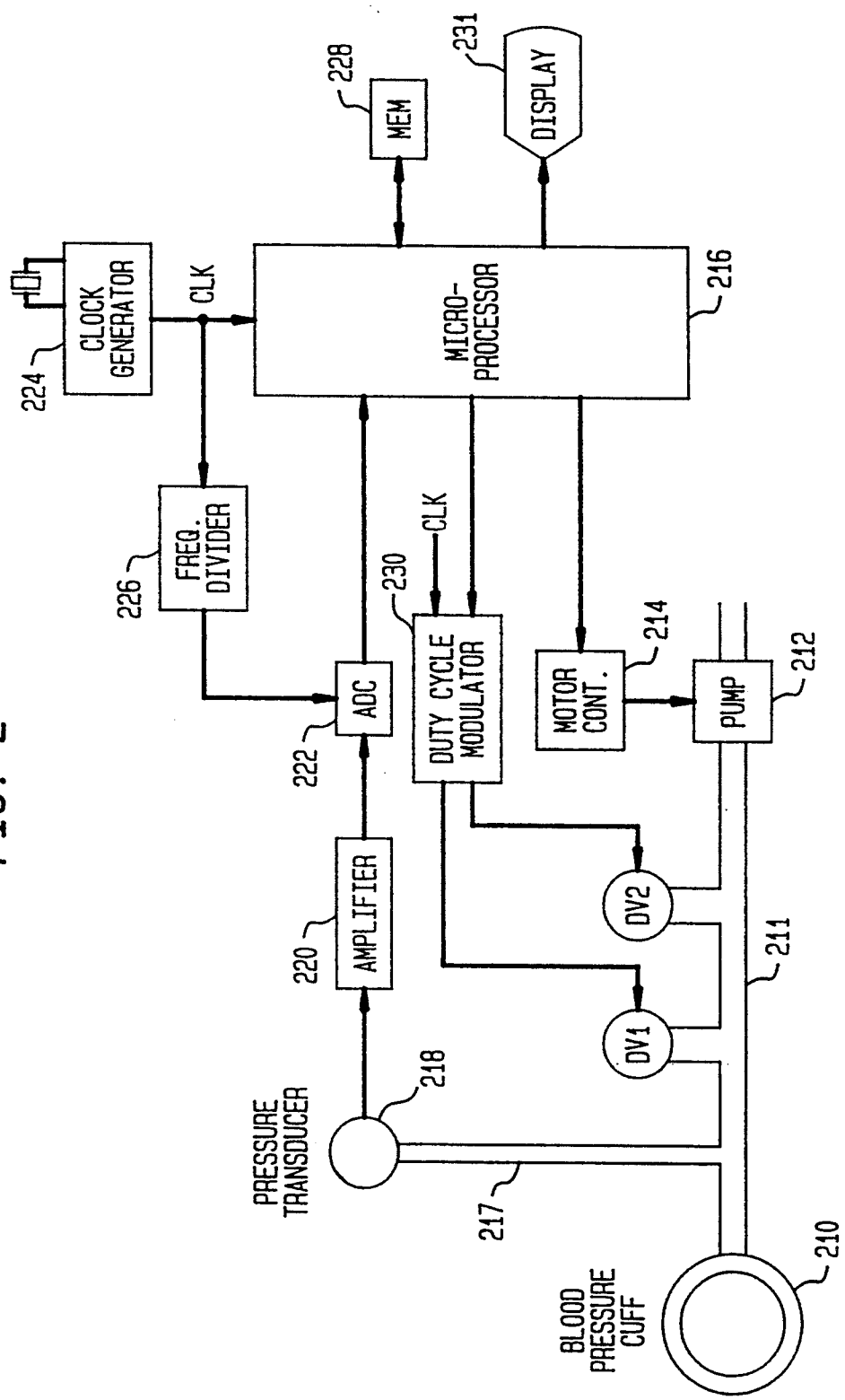
FIG. 2 is a block diagram of an automatic blood pressure measurement system in accordance with the present invention.

FIG. 2 is a block diagram of an exemplary automatic blood pressure gauge according to the present invention. This gauge includes a conventional blood pressure cuff 210 which may be inflated by an electric pump 212 using an air channel 211. The pump motor is turned on and off by a motor controller 214 which is responsive to signals provided by a microprocessor 216. A suitable pump for use in this embodiment of the invention is a diaphragm type, driven by a DC motor.

The cuff is deflated using two digitally controlled solenoid valves, DV1 and DV2. When open, the valve DV1 has a flow rate of 570 standard milliliters per minute (Std ml/min) at 170 mmHg differential pressure, and the valve DV2 has a flow rate of 1,341 Std ml/min at 20 mmHg differential pressure. These valves may be opened and closed in 1.4 milliseconds (ms) and 6 ms, respectively. In this embodiment of the invention, the valves are controlled by a pulse width modulated signal having a set nominal frequency. Only one of the valves is open at any given time during normal operation. By controlling the percentage of time that the valve is opened and closed within each cycle of the control signal, the time-aperture of the valve can be effectively controlled. This time-aperture determines the average rate of airflow through the valve.

The microprocessor 216 controls the valves DV1 and DV2 using a duty cycle modulator 230. The modulator 230, which is described in greater detail below with reference to FIG. 4, produces a 20.35 Hz signal which controls a selected one of the valves DV1 and DV2.

The duty cycle of this signal is controlled to determine the effective aperture of the selected valve, and thus, the rate at which the cuff 210 is deflated.

The microprocessor 216 monitors the air pressure in the cuff using a conventional pressure transducer 218 which is coupled to the air channel 211 via a tube 217. In the exemplary embodiment of the invention, the pressure transducer is of the conventional semiconductor strain gauge type. The signal produced by the transducer 218 is amplified by a low-noise instrument quality amplifier 220 which produces a signal that is applied to an analog to digital converter (ADC) 222. In this embodiment of the invention, the ADC 222 is a 16-bit sigma-delta type analog to digital converter. The ADC 222 produces samples at a rate of approximately 50 Hz. A frequency divider 226 is coupled to receive an 8 MHz clock signal CLK provided by a resonant crystal controlled clock signal generator 224. This signal is divided in frequency as needed to produce the clock signal for ADC 222.

The sampled data pressure signal provided by the ADC 222 is monitored by the microprocessor 216 to stop the pump 212 when the desired initial cuff pressure has been obtained, to control the flow through the deflation valves DV1 and DV2 and to extract, from the pulse signal, the systolic and diastolic blood pressure measurements for the person under test.

The blood pressure measurements are presented on a display device 231. To produce these values, the microprocessor 216 operates under the control of a program stored in a memory 228. The memory 228 also contains cells which may be used for storing temporary data values. In the exemplary embodiment of the invention, the program storage portion of the memory 228 is a read-only memory (ROM) while the data storage portion is a random-access memory (RAM).

The microprocessor 216 captures samples produced by the ADC 222 at a 50 Hz rate. The collected samples are processed in groups of 45 to obtain a noise-reduced cuff pressure signal and its first derivative, representing the actual rate of change of the cuff pressure. These signals have an effective sampling rate of 1.11 Hz. For each sample of this signal, the microprocessor 216 calculates new settings for the deflation valve DV1 or DV2 according to the algorithm shown in FIG. 3.

In the first step in this algorithm, step 310, the initial cuff volume, V, is calculated, one of the deflation valves DV1 or DV2 is selected and an initial flow setting for the selected valve is calculated. The process used to determine the initial cuff volume is shown in FIG. 3a.

Figure 3:
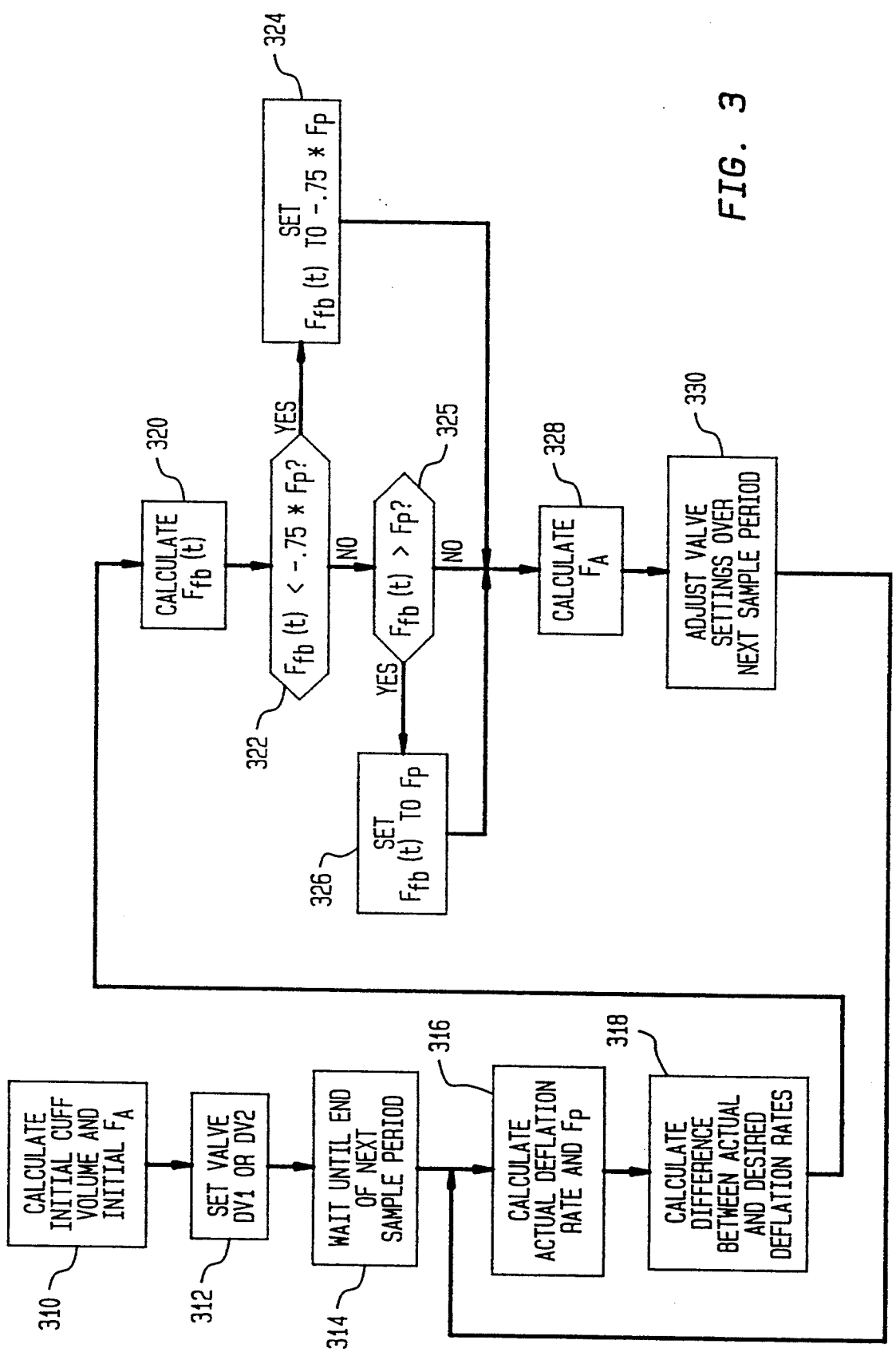
FIGS. 3 and 3a are flow-chart diagrams which are useful for describing the operation of the microprocessor 216.
Figure 3A:
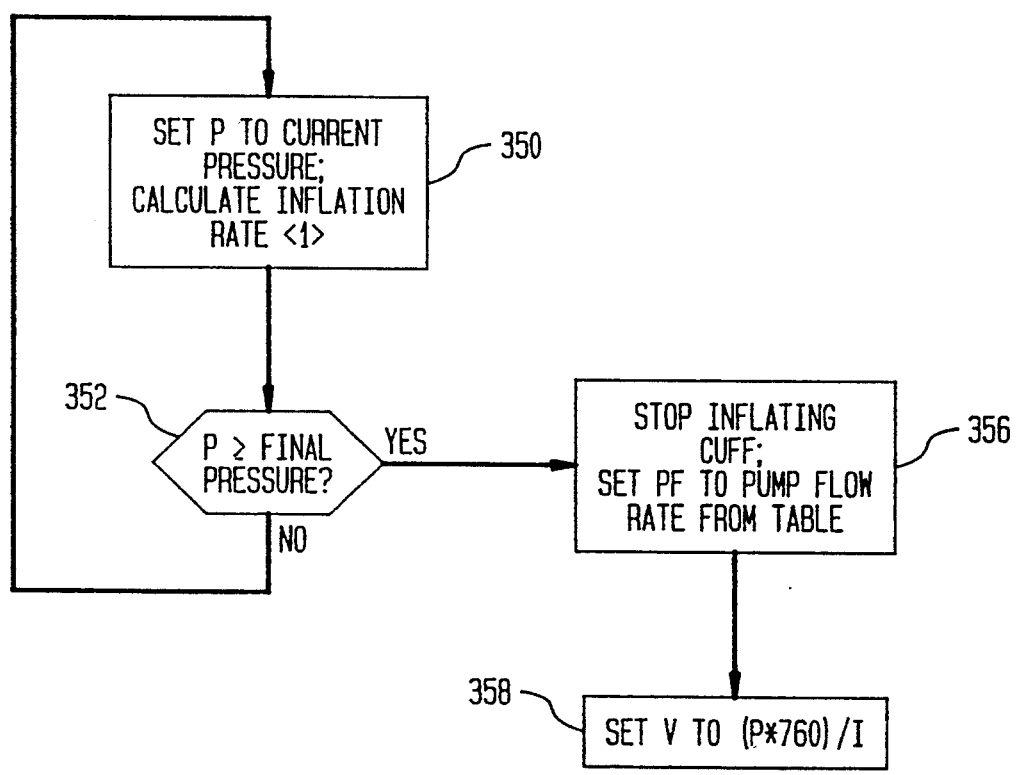

In FIG. 3a at step 350, the microprocessor 216 sets a variable P to the current pressure reading obtained from the pressure transducer 218, and a variable I to the current inflation rate. The inflation rate is a differential pressure value which is obtained by numerically differentiating the pressure signal provided by the transducer 218 over the last 45 sample values. New values of P and I are available at 900 ms intervals as set forth below.

At step 352, the value stored in the variable P is compared to a target final pressure value. If the value in P is less than this target value, then control passes back to step 350.

If, at step 352, the value in the variable P is greater than or equal to the target final pressure value, control is transferred to step 356. In this step, the microprocessor 216 signals the motor controller 214 to stop the pump 212 and, thus, stop inflating the cuff. In addition, the microprocessor 216 uses the current pressure value, as stored in the variable P, as an index into a table which provides the current pump flow rate, PF. At step 358, the values PF and I are substituted into the equation (1) to calculate the initial volume of the cuff.

$$V=(PF*760)/I \tag{1}$$

In this equation PF is the pump flow rate when the cuff pressure has reached its target final pressure value, I is the inflation rate, and the factor 760 represents the pressure of the fluid that is being pumped into the cuff (the flow is specified under standard conditions—1 atmosphere=760 mmHg).

The inflation rate is obtained, as set forth above, from the differential signal value generated by the last group of 45 sample values. The value PF is determined from a table of pump flow versus cuff back pressure (BP). An exemplary table is given as Table 1. In this Table, the pump flow values are divided by a factor of 50. Thus, the table values are PF/50.

TABLE 1

| PF/50 | BP | PF/50 | BP | PF/50 | BP | PF/50 | BP |
|---|---|---|---|---|---|---|---|
| 58 | 0 | 48 | 67 | 41 | 133 | 32 | 200 |
| 57 | 5 | 48 | 72 | 40 | 138 | 32 | 205 |
| 56 | 10 | 47 | 77 | 39 | 143 | 31 | 210 |
| 55 | 15 | 47 | 82 | 38 | 148 | 31 | 215 |
| 54 | 21 | 46 | 87 | 37 | 154 | 31 | 220 |
| 53 | 26 | 46 | 92 | 37 | 159 | 31 | 225 |
| 52 | 31 | 45 | 97 | 36 | 164 | 30 | 230 |
| 51 | 36 | 45 | 102 | 36 | 167 | 30 | 236 |
| 50 | 41 | 44 | 107 | 35 | 174 | 30 | 241 |
| 50 | 46 | 44 | 113 | 35 | 179 | 30 | 246 |
| 49 | 51 | 43 | 118 | 34 | 184 | 29 | 251 |
| 49 | 56 | 43 | 122 | 34 | 189 | 29 | 256 |
| 48 | 61 | 42 | 128 | 33 | 195 | 29 | 261 |

The values in this Table were generated experimentally. To generate a table for a different pump than was used in the exemplary embodiment, the pump is connected to a pressure gauge and to a controllable flow restrictor, such as a needle valve. The output of the needle valve is connected to a flow meter. The flow restrictor is adjusted to generate a given back pressure measurement on the pressure gauge. The flow produced by the pump at that back pressure is measured on the flow meter and recorded. These steps are repeated for all back pressure values to which the pump may be subject in normal operation. To determine the pump flow for a given measured cuff pressure, the table is indexed by the cuff pressure. For values not represented in the Table, the value of the next lower entry is used.

As an alternative to using this table, a single value may be maintained which represents the nominal flow rate of the pump in a range of back pressures likely to be encountered when the cuff volume is to be determined. This value may be obtained experimentally, for example, the average flow rate of the pump at back-pressures between 150 mmHg and 200 mmHg may be a suitable value for adult cuffs.

The initial cuff volume is an important parameter for flexible blood pressure cuffs. This volume will vary with the size of the cuff, the size of the patient's arm or leg, the way in which the cuff is wrapped around the patient's arm or leg and the patient's position while the measurement is being taken. Since, as set forth above, the volume of the cuff is an important factor in achieving a desired deflation rate, it is important that this initial cuff volume be determined accurately.

Once the initial cuff volume has been determined, the initial valve control variable, $F_A$, for the deflation valve DV1 or DV2 is calculated using equations (2) and (3). The initial value of $F_A$ is a combination of a calculated predictive valve control variable, $F_p$, and a feedback term, $F_{fb}$.

$$F_p = V*R*K_p \qquad (2)$$

$$F_A = F_p + F_{fb}(O) \qquad (3)$$

In equation (2), R is the desired deflation rate, for example, 6 mmHg/s and $K_p$ is an experimentally determined factor which produces the desired flow rate for different cuff pressures. The value of this term depends on whether an adult cuff or a neonatal cuff is being used. Exemplary values of $K_p$ for different adult cuff pressure values (ACP) are given below in Table 2. The values in this table are suitable for use with a full range of adult cuffs (e.g. arm to thigh). Table 3 is a list of exemplary values for standard neonatal cuffs in terms of neonatal cuff pressure (NCP). The cuff pressure in both tables is in units of mmHg.

TABLE 2

| $K_P$ | ACP | $K_P$ | ACP | $K_P$ | ACP | $K_P$ | ACP |
|---|---|---|---|---|---|---|---|
| 500 | 0 | 126 | 67 | 64 | 133 | 51 | 200 |
| 500 | 5 | 118 | 72 | 62 | 138 | 51 | 205 |
| 500 | 10 | 108 | 77 | 60 | 143 | 50 | 210 |
| 500 | 15 | 100 | 82 | 59 | 148 | 49 | 215 |
| 450 | 21 | 92 | 87 | 58 | 154 | 49 | 220 |
| 350 | 26 | 84 | 92 | 57 | 159 | 48 | 225 |
| 300 | 31 | 76 | 97 | 56 | 164 | 48 | 230 |
| 250 | 36 | 73 | 102 | 55 | 167 | 47 | 236 |
| 210 | 41 | 69 | 107 | 55 | 174 | 47 | 241 |
| 180 | 46 | 68 | 113 | 54 | 179 | 46 | 246 |
| 160 | 51 | 67 | 118 | 53 | 184 | 45 | 251 |
| 146 | 56 | 66 | 122 | 53 | 189 | 44 | 256 |
| 136 | 61 | 65 | 128 | 52 | 195 | 44 | 261 |

TABLE 3

| $K_P$ | NCP | $K_P$ | NCP | $K_P$ | NCP | $K_P$ | NCP |
|---|---|---|---|---|---|---|---|
| 163 | 0 | 92 | 67 | 64 | 133 | 51 | 200 |
| 163 | 5 | 89 | 72 | 62 | 138 | 51 | 205 |
| 163 | 10 | 86 | 77 | 60 | 143 | 50 | 210 |
| 163 | 15 | 83 | 82 | 59 | 148 | 49 | 215 |
| 163 | 21 | 80 | 87 | 58 | 154 | 49 | 220 |
| 152 | 26 | 77 | 92 | 57 | 159 | 48 | 225 |
| 144 | 31 | 74 | 97 | 56 | 164 | 48 | 230 |
| 132 | 36 | 71 | 102 | 55 | 167 | 47 | 236 |
| 122 | 41 | 69 | 107 | 55 | 174 | 47 | 241 |
| 112 | 46 | 68 | 113 | 54 | 179 | 46 | 246 |
| 101 | 51 | 67 | 118 | 53 | 184 | 45 | 251 |
| 98 | 56 | 66 | 122 | 53 | 189 | 44 | 256 |
| 95 | 61 | 65 | 128 | 52 | 195 | 44 | 261 |

In equation 3, the term $F_{fb}(O)$ is the initial value of a feedback correction term, $F_{fb}(t)$. The algorithm for determining the value of this term while the cuff is being deflated is set forth below. The value of $F_{fb}(O)$ is set to $-0.25 * F_p$ for adult cuffs, and to 0 for neonatal cuffs. This term compensates for an initial drop in cuff pressure at the end of the inflation cycle which is due to the release of thermal energy from the compressed air in the cuff. For neonatal cuffs, the pressure drop caused by this energy release is negligible. Consequently, for these cuffs, the initial feedback term is set to zero.

The value $F_A$ defines the actual valve setting for DV1. If this value is beyond the range of DV1, the value of $F_A$ is multiplied by a scale factor for the use of DV2. This value is translated into duty cycles for one of the two valves DV1 and DV2 as described below with reference to FIG. 4.

The next step in the flow-chart diagram shown in FIG. 3, step 314 is to wait until the start of the next update period. In the exemplary embodiment of the invention, the setting for the valve DV1 or DV2 is updated at 900 ms intervals. During this time, the microprocessor is determining the current cuff pressure value from the 45 most recent pressure sample values provided by the ADC 222. As described above, these sample values are processed to eliminate spurious noise spikes. The result of this processing is a noise-reduced cuff pressure signal.

At step 316, this cuff pressure signal is numerically differentiated over the 45 sample interval to produce a signal representing the actual deflation rate. This step may, for example, subtract each pressure sample value from the preceding sample value and average the results to provide a sampled data deflation rate signal for the interval in which the 45 pressure samples were taken. Also at step 316, the predictive valve setting, $F_p$, is determined by applying equation (2) using the most recent cuff pressure sample as the index into Table 2 or Table 3, depending on whether an adult cuff or a neonatal cuff is being used.

The difference, $R_e$, between the actual deflation rate, calculated at step 316, and the desired deflation rate is calculated at step 318. In this embodiment of the invention, the desired deflation rate is 6 mmHg/s.

At step 320, the microprocessor 216 uses the $R_e$ value calculated in step 318 and the equation (4) to compute a feedback term, $F_{fb}(t)$, for the current time interval, t.

$$F_{fb}(t) = (V*R_e*K_G) + F_{fb}(t-1) \qquad (4)$$

In the equation (4), $K_G$ is a feedback gain factor. This factor is experimentally determined to produce a desired loop time constant for the feedback loop. In the exemplary embodiment of the invention, this factor has a value of 0.31. This gain factor enables the loop to respond to changes in the volume of the cuff caused by patient motion but to be relatively insensitive to the pulse signal component of the pressure signal.

The initial volume factor, V, in the first term of the equation normalizes the transient response of the feedback controller for different cuff volumes. Because of this factor, cuffs having relatively large initial volumes are allowed to have relatively large feedback correction terms while cuffs having relatively small initial volumes are only allowed to have small feedback correction terms. As described above, the initial cuff volume depends on a number of factors such as the size of the patient's arm and how the cuff is wrapped around the arm.

The feedback term $F_{fb}(t)$, as defined by equation (4), is an integrated value since the first term in equation (4), $(V*R_e*K_G)$, is summed with the value of the feedback term from the previous time period, $F_{fb}(t-1)$, to obtain the feedback term for the current time period, $F_{fb}(t)$. In addition, the amplitude of the feedback term is limited as shown in steps 322 through 326 of FIG. 3 based on the value of the predictive valve setting, $F_p$. Step 322 determines if the calculated feedback term, $F_{fb}(t)$, is less than $-0.75*F_p$. If so, then at step 324 the value $-0.75*F_p$ is substituted for $F_{fb}(t)$. Otherwise, step 325 determines if $F_{fb}(t)$ is greater than $F_p$. If this condition is met, step 326 assigns the value $F_p$ to $F_{fb}(t)'$. The result of these calculations is a final feedback term, $F_{fb}(t)'$. This term is summed with the predictive valve setting $F_p$ as shown in equation (5) to obtain a new actual valve setting $F_A$.

$$F_A = F_p + F_{fb}(t)' \quad (5)$$

The feedback term is limited to prevent large correction terms from being applied when there is a large transient change in the actual cuff deflation rate. If, for example, the cuff volume is changed because the patient flexed his or her arm, there may be, for a short time interval, a relatively large difference between the actual deflation rate and the desired deflation rate. If the system corrects for this difference in a single step, there would be a continuing error when the flexed muscle is relaxed. This continuing error is caused by the integral nature of the feedback term. In the exemplary embodiment of the invention, the magnitude of these continuing errors is reduced by limiting the amount by which the feedback term may change.

The feedback term $F_{fb}(t)'$ tends to match the actual deflation rate to the desired rate. It compensates for volume changes in the cuff during the deflation process and for valve and pump flow inaccuracies. Since the gain of the feedback loop is relatively low and since the feedback correction term is updated only once every 900 ms, it does not tend to interfere with the pulse signals. This occurs because the pulse signal frequencies of, for example, 0.5 to 6 Hz, are outside of the range of frequencies that can be tracked by the feedback loop.

If the actual valve setting calculated in step 328 is different from the current valve setting, step 330 changes to the new valve setting gradually over the next 900 ms sample interval. This step is described in greater detail below, with reference to FIG. 5. Following step 330, the program branches back to step 316 to begin the calculations that determine the valve settings for the next interval.

Figure 4:
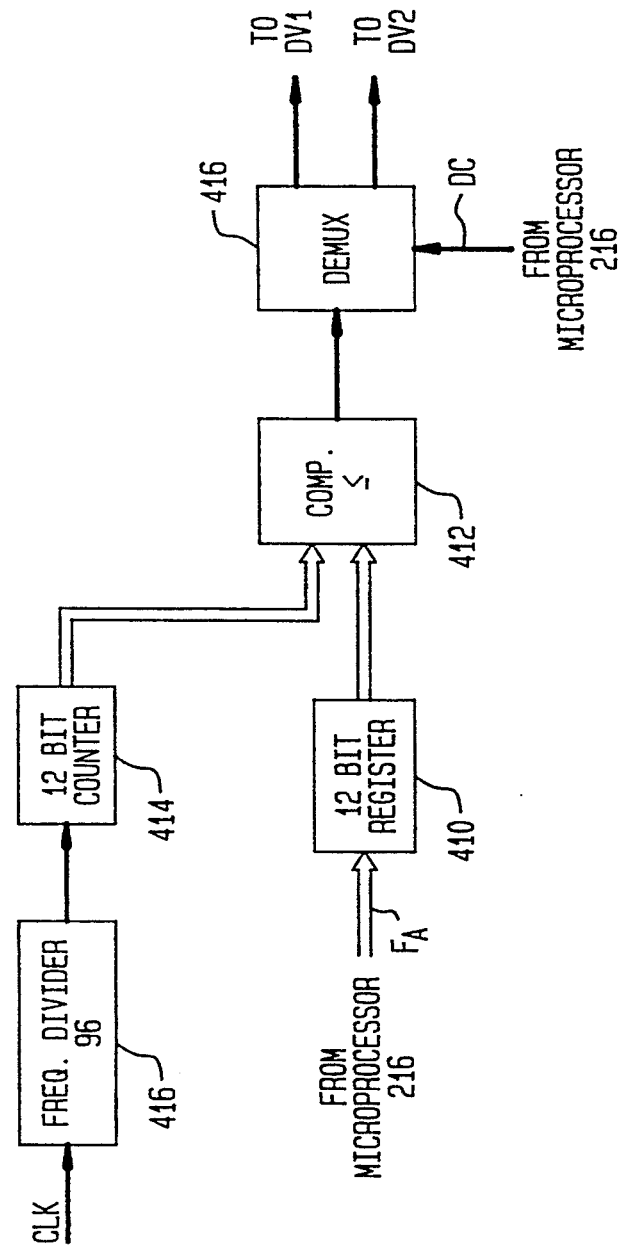
FIG. 4 is a block diagram of circuitry suitable for use as the duty cycle modulator shown in FIG. 2.

FIG. 4 shows exemplary circuitry which may be used as the duty cycle modulator 230 shown in FIG. 2. In this circuitry, a new 12-bit data value, representing the most recently calculated value for $F_A$, is loaded into a register 410 by the microprocessor 216, to change the time-aperture of the currently selected valve DV1 or DV2. As described above, these valves are solenoid valves which may be opened or closed, responsive to a control signal. The valve DV1 or DV2 is open when its control signal is logic-high and closed when its control signal is logic-low.

The valves DV1 and DV2 are selected so that, when both valves are open, the flow through DV2 is approximately eight times the flow through DV1. In this embodiment of the invention, valve DV1 is selected when low valve flow rates are desired and DV2 is selected to achieve higher valve flow rates.

The control signal for the selected valve is provided by a comparator 412. This comparator compares the value held in the register 410 with a value provided by a 12-bit counter 414. The clock input signal to the counter is the 8 MHz signal CLK divided, in frequency, by a factor of 96 by a frequency divider 416 to produce a clock signal having a frequency of 83.33 KHz. Responsive to this clock signal, the counter cycles through all of its 4,096 values 20.35 times per second.

The comparator 412 is configured so that it produces a logic-high output signal when the value provided by the register 410 is less than or equal to the value provided by the counter 414 and produces a logic-low output signal otherwise. This signal is provided to a demultiplexer 416, which, responsive to a signal DC provided by the microprocessor 216, routes the control signal to either DV1 or DV2.

Figure 5:
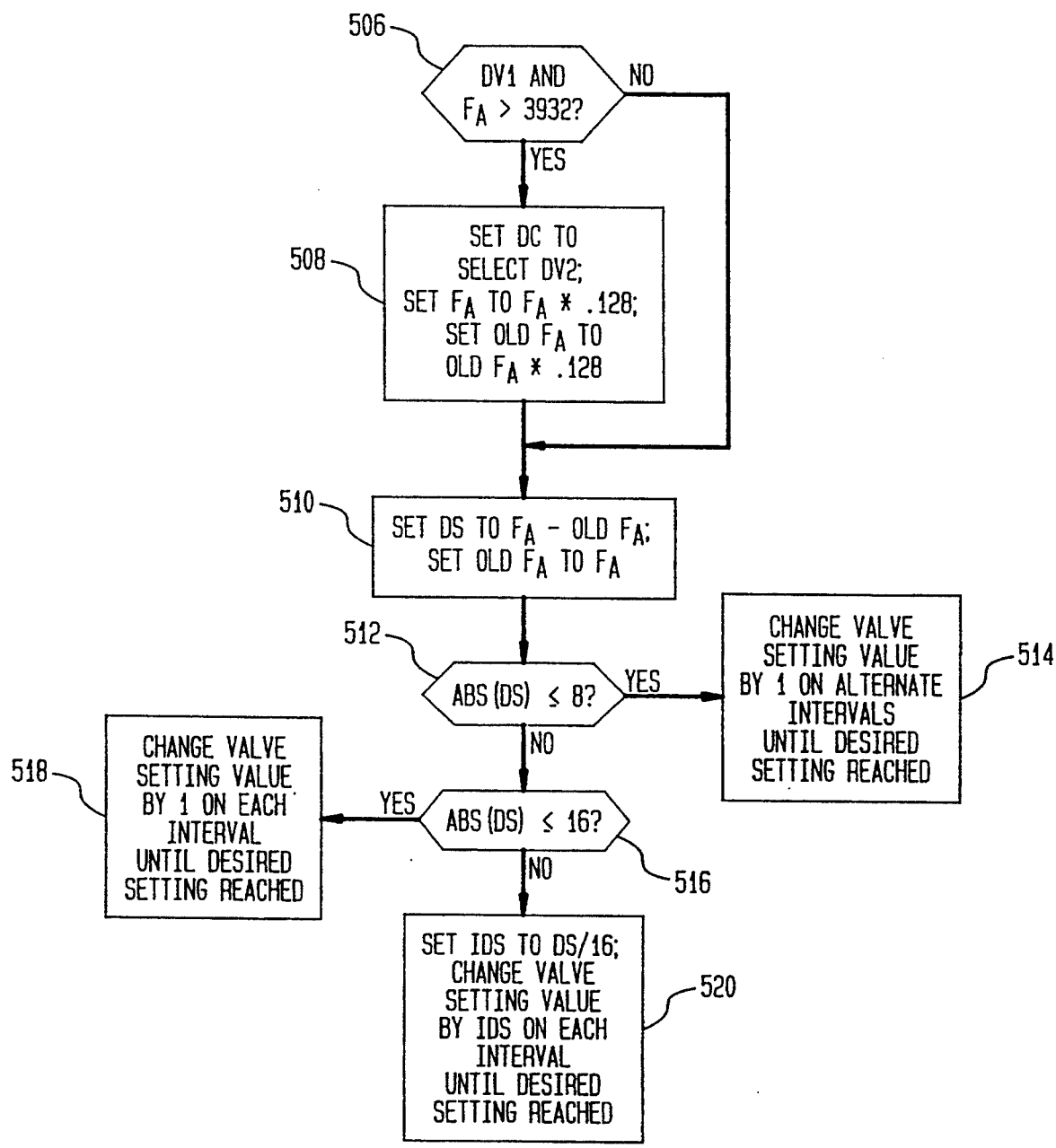
FIG. 5 is a flow-chart diagram which illustrates how the microprocessor shown in FIG. 2 controls the duty cycle modulator shown in FIG. 4.

When the process shown in FIG. 3 selects and adjusts the valve DV1 or DV2 at step 330, it does not make the entire adjustment in one step. Instead, it adjusts the valves gradually over the next 900 ms interval. This is done to prevent artifact pulses which may occur if the flow were to change suddenly. FIG. 5 is a flow-chart diagram which illustrates the method by which the microprocessor 216 controls the valves DV1 and DV2 to in response to a new valve setting calculated at step 328.

In the exemplary embodiment of the invention, new values for the valve setting are calculated at 900 ms intervals. The valve settings, however, are each in terms of a duty cycle of a square wave having a period of 49 ms (i.e. 1/20.35 Hz) and the microprocessor can update the value held in the register 410, shown in FIG. 4, at the end of each 49 ms interval. Thus, during each 900 ms interval, the settings for the selected deflation valve DV1 or DV2 can be adjusted as many as 18 times.

The first step in the process which adjusts the settings for these valves, step 506, selects which of the two valves, DV1 or DV2 is to be adjusted. When low flow settings are required to provide the desired deflation rate, such as when a small cuff is deflated at high pressure, DV1 is selected. When higher flow settings are desired, such as when a relatively large cuff is deflated at low pressure, DV2 is selected.

When valve DV1 is selected and the value $F_A$ applied to the register 410 is greater than 3,932, step 508 is executed. In this step, the microprocessor 216 changes the signal DC, which is applied to the demultiplexer 416 of FIG. 4, to select valve DV2. At the same time, the microprocessor 216 multiplies the current valve setting value (OLD $F_A$) and the new valve setting value ($F_A$) by 0.128. It then stores the new value for OLD $F_A$ into the register 410. These steps cause an immediate switch to valve DV2 from valve DV1.

Step 510 is executed after step 508, or after step 506 if the comparison in 506 is negative. Step 510 subtracts the new valve setting value, $F_A$, from the current valve setting value, OLD $F_A$, to obtain a value, DS, which indicates the amount by which the current setting must be changed to reach the new setting. Step 512 determines if the absolute value of DS is less than or equal to 8. If so, then at step 514, the microprocessor 216 invokes a procedure which changes the 12 bit number stored in the register 410 of FIG. 4 in unit steps at intervals corresponding to alternate ones of the 20.35 Hz pulses until the desired setting value is reached.

If, at step 512, the absolute value of DS is greater than 8, then step 516 is executed. This step determines if DS is less than or equal to 16. If it is, then step 518 is executed. This step invokes a procedure which changes the 12-bit value stored in the register 410 in unit steps for each pulse of the 20.35 Hz signal until the desired setting value is reached.

If, at step 516, the absolute value of DS is greater than 16, step 520 is executed. This step divides the value DS by 16 to produce a value IDS. Step 520 then invokes a procedure which changes the value in the register 410 by IDS for each pulse of the 20.35 Hz signal until the desired valve setting is reached.

It is noted that the amount by which the valve setting is to be changed may be either positive or negative.

Accordingly, in FIG. 5 and the accompanying description, any change in the value held in register 410 may be positive or negative.

In the exemplary deflation control system described above, a blood pressure cuff, which has been inflated to a preset initial pressure and has an initial volume of fluid, is deflated at a substantially constant rate by controlling the time-aperture of two deflation valves. The apparatus which controls these valves monitors the pressure in the cuff and periodically changes the time-aperture of the valves to maintain the desired deflation rate. This control apparatus uses a table which relates the current cuff pressure to a predictive valve setting to produce a desired deflation rate for the next interval. A feedback control loop is also employed to modify the actual valve settings to be used within predefined limits to maintain the desired deflation rate. The feedback signals are normalized by the initial cuff volume so that the time constant of the loop is substantially independent of the cuff volume.

While this invention has been described in terms of an exemplary embodiment, it is contemplated that it may be practiced as outlined above within the scope of the appended claims.

The invention claimed is:

1. Apparatus suitable for use in an automatic blood pressure gauge having a cuff which contains a pressurizing fluid, comprising:
   pressure measuring means, coupled to the cuff, for measuring an instantaneous pressure level of the pressurizing fluid in the cuff at a plurality of instants corresponding to starting points of a respective plurality of time periods to produce a pressure signal;
   valve means, coupled to the cuff and having an aperture which may be changed in response to an applied control signal, for venting the pressurizing fluid from the cuff at a flow rate determined by said control signal; and
   flow control means, communicating with said pressure measuring means so as to be responsive to the pressure signal, for generating successive predictive values for the control signal applied to the valve means at respective ones of the instants corresponding to the starting points of the plurality of time periods, to produce a reduction in the instantaneous pressure level of the pressurizing fluid in the cuff during a time interval which includes the plurality of time periods, and at a rate which approximates a predetermined desired rate of pressure reduction;
   and wherein said flow control means includes a table of possible predictive values for the control signal, each value in said table being associated with a respective value of the pressure signal; and
   means for indexing the table of possible predictive values using the pressure signal to obtain a next predictive value of the control signal to be used during a corresponding next one of the plurality of time periods.

2. The apparatus of claim 1, wherein the cuff holds an initial volume of the pressurizing fluid, the valve means is responsive to a valve setting signal derived from the control signal to control the aperture of the valve means, and the flow control means further includes means for generating the valve setting signal, comprising means for multiplying the control signal value obtained from the table by a value representing the initial volume of the pressurizing fluid and by the predetermined desired rate of pressure reduction to generate the predictive valve setting signal for the valve means.

3. The apparatus of claim 2, further comprising:
   means for generating a feedback correction signal including:
   means, responsive to the pressure signal, for generating a deflation rate signal which represents the rate at which the pressure of the pressurizing fluid in the cuff is being reduced;
   means for subtracting the deflation rate signal from the predetermined desired rate of pressure reduction to generate a deflation rate error signal;
   means for multiplying the deflation rate error signal by the value representing the initial volume of the pressurizing fluid in the cuff and by a predetermined gain factor to produce a feedback signal;
   means for accumulating the feedback signal over successive time periods; and
   means for limiting the value of the accumulated feedback signal to minimum and maximum values in a predetermined proportion to the predictive valve setting signal to generate the feedback correction signal; and
   means for adding the predictive valve setting signal to the feedback correction signal to generate the valve setting signal which controls the time-aperture of the valve means.

4. The apparatus of claim 1, wherein:
   the pressure measuring means further includes means, responsive to the pressure signal, for generating a deflation rate signal which represents a rate at which the instantaneous pressure level of the pressurizing fluid in the cuff is being reduced; and
   the flow control means further includes feedback control means, responsive to the differential rate between the deflation rate signal and the predetermined desired rate of pressure reduction, for adjusting the predictive values for the control signal to decrease the differential rate between the deflation rate signal and the predetermined desired rate of pressure reduction.

5. The apparatus of claim 4 wherein the feedback control means includes:
   means for generating an adjustment signal for the control signal including:
   means for generating a feedback control signal which is proportional to the differential rate between the deflation rate signal and the predetermined desired rate of pressure reduction;
   means for accumulating values of the feedback control signal over several of the time periods to produce an accumulated feedback control signal; and
   means for limiting the accumulated feedback control signal to be within predetermined minimum and maximum values to generate the adjustment signal; and
   means for adding the adjustment signal to the control signal to produce an adjusted control signal which is applied to the valve means to control the time-aperture of the valve means.

6. The apparatus of claim 5 wherein the means for generating the feedback control signal includes means for multiplying the differential rate between the deflation rate signal and the predetermined desired rate of pressure reduction by a value representing an initial volume of the pressurizing fluid in the cuff and by a predetermined loop gain factor.

7. The apparatus of claim 1 wherein the valve means includes:
   a solenoid valve; and
   modulation means, coupled to the solenoid valve, for generating a pulse signal having a duty cycle which is proportional to the predictive value of the control signal, where the duty cycle of the pulse signal controls the time-aperture of the valve means.

8. The apparatus of claim 7 wherein:
   the valve means includes a further solenoid valve having a different maximum flow than said solenoid valve; and
   the modulating means includes means, responsive to the control signal, for selecting one of said solenoid valve and said further solenoid valve for venting the pressurizing fluid from the cuff.

9. The apparatus of claim 8 wherein:
   each of the plurality of time periods includes a plurality of sub-intervals; and
   the flow control means includes means for implementing any change in the control signal incrementally over the sub-intervals of a subsequent one of the plurality of time periods.

10. Apparatus suitable for use in an automatic blood pressure gauge having a cuff which contains a pressurizing fluid, comprising:
    pressure measuring means, coupled to the cuff, for measuring an instantaneous pressure level of the pressurizing fluid in the cuff at a plurality of instants corresponding to starting points of a respective plurality of time periods to produce a pressure signal;
    valve means, coupled to the cuff and having an aperture which may be changed in response to an applied control signal, for venting the pressurizing fluid from the cuff at a flow rate determined by said control signal;
    volume determining means coupled to the pressure measuring means and responsive to the pressure signal produced thereby for determining an initial volume of the pressurizing fluid in the cuff and;
    flow control means, communicating with said pressure measuring means so as to be responsive to the pressure signal, and communicating with said volume determining means so as to be responsive to the determined initial volume for generating successive predictive values for the control signal applied to the valve means at respective ones of the instants corresponding to the starting points of the plurality of time periods, to produce a reduction in the instantaneous pressure level of the pressurizing fluid in the cuff during a time interval which includes the plurality of time periods, and at a rate which approximates a predetermined desired rate of pressure reduction.

11. The apparatus of claim 10 further including means coupled to the cuff for inflating the cuff with the pressurizing fluid, wherein the means for determining the initial volume of the pressurizing fluid in the cuff includes:
    means, responsive to the pressure signal for generating an inflation rate signal having an instantaneous value which represents a corresponding instantaneous inflation rate of the cuff;
    means, responsive to the pressure signal for generating a flow rate signal having an instantaneous value which represents a corresponding instantaneous rate of flow of the pressurizing fluid provided by the means for inflating the cuff; and
    means, responsive to the instantaneous value of the flow rate signal and to the instantaneous value of the inflation rate signal when the pressure signal indicates that a desired pressure level has been achieved, for determining the initial volume of pressurizing fluid in the cuff.

12. The apparatus of claim 10 further including pump means for providing the pressurizing fluid to inflate the cuff, wherein the means for determining the initial volume of the pressurizing fluid in the cuff includes:
    means, responsive to the pressure signal, for generating an inflation rate signal having an instantaneous value which represents a corresponding instantaneous inflation rate of the cuff;
    means, coupled to the pump means, for providing a flow rate signal, representing a flow rate for the pressurizing fluid provided by the pump means to the cuff; and
    means, responsive to the pressure signal, for dividing the flow rate signal by the instantaneous value of the inflation rate signal when the pressure signal indicates that a desired pressure level has been achieved, for determining the initial volume of the pressurizing fluid in the cuff.

13. A method of deflating a cuff of an automatic blood pressure gauge in a controllable manner, the cuff containing a pressurizing fluid, the method comprising the steps of:
    a) measuring an instantaneous pressure level of the pressurizing fluid in the cuff at a plurality of instants corresponding to starting points of a respective plurality of time periods to produce a pressure signal;
    b) determining an initial volume of the pressurizing fluid in the cuff;
    c) generating, at the instants corresponding to the starting points of the plurality of time periods, a respective plurality of successive predictive values for a control signal responsive to the measured pressure levels, wherein the successive predictive values of the control signal determine a rate at which the measured pressure levels are decreasing in the cuff during the respective time periods, so as to reduce the pressure of the pressurizing fluid in the cuff at a rate which approximates a predetermined desired rate of pressure reduction; and
    d) controllably venting the pressurizing fluid from the cuff in response to the control signal.

14. The method of claim 13 wherein:
    each of the plurality of time periods includes a plurality of sub-intervals; and
    the step d) includes the step of implementing any change in the predictive value of the control signal incrementally over the sub-intervals of a subsequent one of the plurality of time periods.

15. The method of claim 13 wherein the step d) includes the step of indexing a table of possible predictive values for the control signal, using the measured instantaneous pressure level, to obtain the predictive control signal value to be used during a next one of the plurality of time periods, wherein each of the possible predictive values in the table is associated with a respective pressure level of the pressurizing fluid in the cuff which produces the desired flow rate.

16. The method of claim 15, wherein the cuff holds an initial volume of the pressurizing fluid and is responsive to a valve setting signal derived from the control signal to control the rate at which the measured pressure levels are decreased in the cuff, and the step d) further includes a method of generating the valve setting signal comprising the steps of:

multiplying the predictive control signal value obtained from the table by a value representing the initial volume of the pressurizing fluid in the cuff and by the predetermined desired rate of pressure reduction to generate a desired valve setting signal;

generating a feedback correction signal including the steps of:

calculating, from the pressure signal, a deflation rate signal which represents the rate at which the measured pressure levels are decreasing in the cuff;

subtracting the deflation rate signal from the predetermined desired rate of pressure reduction to generate a deflation rate error signal;

multiplying the deflation rate error signal by a value representing the initial volume of the pressurizing fluid in the cuff and by a predetermined loop gain factor to produce a feedback signal;

accumulating the feedback signal over successive ones of the plurality of time periods to produce an accumulated feedback signal; and limiting the accumulated feedback signal to minimum and maximum value which are in a predetermined proportion to the desired valve setting signal to generate the feedback correction signal; and adding the desired valve setting signal to the feedback correction signal to generate the valve setting signal.

17. The method of claim 13 further including the steps of:

generating, from the measured pressure levels, a signal representing the rate at which the measured pressure levels are decreasing in the cuff;

subtracting the signal representing the rate at which pressure is decreasing in the cuff from the predetermined desired rate of pressure reduction to produce a difference signal; and adjusting the generated plurality of predictive values of the control signal to decrease the difference signal in magnitude.

18. The method of claim 17 wherein the step of adjusting the generated plurality of predictive control signal values includes the steps of:

generating an adjustment signal for the control signal including the steps of:

generating a feedback control signal which is proportional to a difference between the signal representing the rate at which pressure is decreasing in the cuff and the predetermined desired rate of pressure reduction;

accumulating the feedback control signal over several of the plurality of time periods to produce an accumulated feedback control signal; and limiting the accumulated feedback control signal to be within predetermined minimum and maximum values to produce the adjustment signal; and adding the adjustment signal to the control signal to produce an adjusted control signal which determines a rate at which the pressurizing fluid is vented from the cuff.

19. Apparatus for measuring the initial volume of pressurizing fluid in a cuff of a blood pressure gauge, comprising:

pump means coupled to the cuff for inflating the cuff with the pressurizing fluid;

pressure measuring means coupled to the cuff for measuring an instantaneous pressure of the pressurizing fluid in the cuff to generate a pressure signal;

inflation rate determining means coupled to the pressure measuring means and responsive to the pressure signal for calculating, from the pressure signal, an inflation rate signal representing a rate at which the instantaneous pressure of the pressurizing fluid in the cuff is increasing as the cuff is inflated by the pump means;

flow rate determining means coupled to the pressure measuring means and responsive to the pressure signal, for generating a flow rate signal, representing an instantaneous rate of flow of the pressurizing fluid into the cuff; and means coupled to both the inflation rate and flow rate determining means and responsive to both the inflation rate and flow rate signals, for dividing the flow rate signal by the inflation rate signal to produce a value representing the instantaneous volume of the pressurizing fluid in the cuff.

20. Apparatus for measuring the initial volume of pressurizing fluid in a cuff of a blood pressure gauge, comprising:

pump means coupled to the cuff for inflating the cuff with the pressurizing fluid;

pressure measuring means coupled to the cuff for measuring an instantaneous pressure of the pressurizing fluid in the cuff to generate a pressure signal;

inflation rate determining means coupled to the pressure measuring means and responsive to the pressure signal for calculating, from the pressure signal, an inflation rate signal representing a rate at which the instantaneous pressure of the pressurizing fluid in the cuff is increasing as the cuff is inflated by the pump means;

flow rate determining means, coupled to the pump means, for providing a flow rate signal, representing a flow rate for the pressurizing fluid provided by the pump means to the cuff; and means coupled to both the inflation rate determining and flow rate indicator means and responsive to both the inflation rate and flow rate signals, for dividing the flow rate signal by the inflation rate signal to produce a value representing the instantaneous volume of the pressurizing fluid in the cuff.

21. Apparatus suitable for use in an automatic blood pressure gauge having a cuff which contains a pressurizing fluid the apparatus, comprising:

pressure measuring means, coupled to the cuff, for measuring instantaneous pressure levels of the pressurizing fluid in the cuff to provide a pressure signal;

valve means, coupled to the cuff and having an aperture which may be changed in response to a control signal, for venting the pressurizing fluid from the cuff at a rate determined by the control signal; and feedback control means coupled to the pressure measuring means and responsive to the pressure signal for generating said control signal to control the venting of the pressurizing fluid from the cuff to maintain a desired rate of pressure reduction, said feedback control means including:

deflation rate determining means, coupled to receive said pressure signal, for calculating a deflation rate signal representing an instantaneous rate of pressure reduction in the cuff;

differencing means coupled to the deflation rate determining means and responsive to the deflation rate signal for calculating a difference between the deflation rate signal and the desired rate of pressure reduction to produce a deflation rate difference signal; and means coupled to the differencing means and responsive to the difference signal for multiplying the deflation rate difference signal by a value representing an initial volume of the pressurizing fluid in the cuff to generate said control signal.

* * * * *

UNITED STATES PATENT AND TRADEMARK OFFICE
CERTIFICATE OF CORRECTION

PATENT NO. : 5,337,751

DATED : August 16, 1994

INVENTOR(S) : Newell et al.

It is certified that error appears in the above-identified patent and that said Letters Patent is hereby corrected as shown below:

Column 15
   Line 3: delete "decreased" insert --decreasing--.

Column 16
   Line 42: delete "determining" and insert --indicator--.

Signed and Sealed this

Twenty-fifth Day of October, 1994

Attest:

BRUCE LEHMAN

*Attesting Officer*          *Commissioner of Patents and Trademarks*